(12) United States Patent
Chae

(10) Patent No.: US 10,743,745 B2
(45) Date of Patent: Aug. 18, 2020

(54) ENDOSCOPE

(71) Applicant: THE CATHOLIC UNIVERSITY OF KOREA INDUSTRY-ACADEMIC COOPERATION FOUNDATION, Seoul (KR)

(72) Inventor: Hiun Suk Chae, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 290 days.

(21) Appl. No.: 15/111,656

(22) PCT Filed: Jan. 27, 2015

(86) PCT No.: PCT/KR2015/000845
§ 371 (c)(1),
(2) Date: Jul. 14, 2016

(87) PCT Pub. No.: WO2015/115773
PCT Pub. Date: Aug. 6, 2015

(65) Prior Publication Data
US 2016/0374537 A1    Dec. 29, 2016

(30) Foreign Application Priority Data

Jan. 28, 2014  (KR) .................. 10-2014-0010841
Mar. 24, 2014  (KR) .................. 10-2014-0033951

(51) Int. Cl.
*A61B 1/00* (2006.01)
*A61B 1/012* (2006.01)
(Continued)

(52) U.S. Cl.
CPC ...... *A61B 1/00089* (2013.01); *A61B 1/00101* (2013.01); *A61B 1/00137* (2013.01);
(Continued)

(58) Field of Classification Search
CPC ............ A61B 1/00089; A61B 1/00101; A61B 1/00137; A61B 1/012; A61B 1/31;
(Continued)

(56) References Cited

U.S. PATENT DOCUMENTS 5,788,715 A * 8/1998 Watson, Jr. ...... A61B 17/12013
606/140
2013/0231531 A1* 9/2013 Naito ................. A61B 1/00089
600/109

FOREIGN PATENT DOCUMENTS

JP     08-052148 A    2/1996
JP     3017451 B2    12/1999
(Continued)

OTHER PUBLICATIONS

English Translation of JP 2002301011A is attached.*
(Continued)

*Primary Examiner* — Ryan N Henderson
*Assistant Examiner* — Pamela F Wu
(74) *Attorney, Agent, or Firm* — Sughrue Mion, PLLC

(57) ABSTRACT

The present invention relates to an endoscope. The present invention may include an endoscope main body; and a guide cap that is mounted to be fixed to a front end of the endoscope main body when inserting the endoscope main body into a human body and slides to protrude toward the front of the endoscope main body when withdrawing the endoscope main body inserted into the human body. An object of the present invention is to facilitate insertion of the endoscope by freely varying a length of the cap from the front end of the endoscope, and to enhance the detection rate of polyp.

6 Claims, 6 Drawing Sheets

(51) Int. Cl.
 *A61B 1/31* (2006.01)
 *A61B 1/32* (2006.01)
 *A61M 25/09* (2006.01)
 *A61B 17/12* (2006.01)

(52) U.S. Cl.
 CPC ............... *A61B 1/012* (2013.01); *A61B 1/31* (2013.01); *A61B 1/32* (2013.01); *A61M 25/09* (2013.01); *A61B 2017/12018* (2013.01)

(58) Field of Classification Search
 CPC ..... A61B 1/32; A61B 1/0008; A61B 1/00085; A61B 1/00087; A61B 1/00098; A61B 1/00131; A61B 1/00135; A61B 1/0014; A61B 1/0125; A61B 1/018
 USPC ............... 600/127, 104, 129, 106–107, 114; 606/46, 139–140
 See application file for complete search history.

(56) References Cited

FOREIGN PATENT DOCUMENTS

| | | | |
|---|---|---|---|
| JP | 2002301011 A | * 10/2002 | ......... A61B 1/00089 |
| JP | 3686876 B2 | 6/2005 | |
| WO | 96/24292 A1 | 8/1996 | |

OTHER PUBLICATIONS

Iida (JPH0852148) english translation through Espacenet. Titled "Endoscope Banding Device". Original JP document provided by applicant. (Year: 1996).*

International Search Report of PCT/KR2015/000845 dated May 8, 2015 [PCT/ISA/210].

\* cited by examiner

ENDOSCOPE

CROSS-REFERENCE TO RELATED APPLICATIONS

This application claims benefit of priority to Korean Patent Application No. 10-2014-0010841 filed on Jan. 28, 2014 and No. 10-2014-0033951 filed on Mar. 24, 2014 in the Korean Intellectual Property Office, the disclosure of which is incorporated herein by reference in its entirety.

BACKGROUND

1. Field

The present invention relates to an endoscope, and more particularly, to an endoscope having a structure that is capable of smoothly performing insertion, while securing the visual field of the endoscope, even when a cap is coupled.

2. Description of Related Art

It is important to find cells that may proceed to a colorectal cancer, such as polyps of large intestine of internal organs of the human body. To attain this end, in general, colonoscopy is performed, and to find a cell, such as a polyp, it is very important to increase the detection rate of polyp.

However, because the inner walls of the large intestine are folded and curved, there was a difficulty in smoothly taking pictures of the inner wall surfaces using the endoscope. When taking pictures of the inner walls of the large intestine folded in a zigzag manner at the time of the conventional large intestine endoscopy, the detection rate of polyps may be lowered by about 20% to 30%. Therefore, in order to solve this problem, a tubular shape made of a transparent material was coupled to a front end of the endoscope. When taking pictures of the endoscope in the status in which the cap is coupled in this way, it is possible to take pictures of the inner walls, while pushing to flatten the winding large intestine inner walls away using a cap.

However, when inserting the endoscope while the cap is coupled, there was a problem in which the visual field of the endoscope may be narrowed, and time taken for insertion may become longer. In particular, in the case of the large intestine endoscope, at the time of insertion, there is a need for a cap in which a length of the endoscope front end to the front end of the cap is long, and conversely, at the time of recovery of the endoscope, there is a need for a cap in which a length from the front end of the endoscope to the front end of the cap is short. However, the length of the cap may vary depending on proficiency and preference of physician who performs procedure of colonoscopy. Therefore, it is necessary to develop an endoscope having a structure that is capable of smoothly performing the insertion, while ensuring the visual field of the endoscope even when the cap is coupled.

Accordingly, to solve the aforementioned problems of conventional techniques, an object of the present invention is to provide an endoscope that can increase the detection rate of polyp, by controlling the length of the cap depending on various situations of practitioner at the time of the endoscopy, and can smoothly insert the endoscope, while ensuring the visual field of the endoscope even when the cap is coupled.

SUMMARY

An aspect of the present may provide an endoscope which includes an endoscope main body; and a guide cap that is mounted to be fixed to a front end of the endoscope main body when inserting the endoscope main body into a human body and slides to protrude toward the front of the endoscope main body when withdrawing the endoscope main body inserted into the human body.

An outer cap may be mounted on the front end of the endoscope main body, and the guide cap slides inside the endoscope main body.

A supporting means may be provided in the outer cap to support the rear end of the guide cap, in a status in which the guide cap slides forward.

The endoscope may further include a guide wire which is connected to the guide cap through a guide channel formed in the endoscope main body, to make the guide cap slide forward.

The endoscope may further include an interlocking wire, both end portions of which are connected to each of the guide cap and the guide wire.

The endoscope further includes a guide wire that passes through the guide channel formed in the endoscope main body and is connected with the guide cap to make the guide cap slide forward, and a catching arm may be formed in the guide wire to be inclined forward.

A catching portion is formed at the front end of the catching arm, and the endoscope may further include an interlocking wire, both end portions of which are connected to each of the guide cap and the catching portion.

A catching portion is formed at the front end of the catching arm, and a plurality of cap holes is formed at the front end of the guide cap in an outer peripheral direction, and the catching portion may be caught by the cap hole.

According to another aspect of the present invention, the endoscope according to the present invention includes an endoscope main body; an inner cap mounted on a front end of the endoscope main body; and a guide cap that slides on the outside of the inner cap, is mounted to be fixed to a front end of the endoscope main body when inserting the endoscope main body into the human body, and slides to protrude to the front of the endoscope main body when withdrawing the endoscope main body inserted into the human body.

The inner surface of the guide cap may be provided with a locking protrusion that is selectively caught by catching grooves formed on the outer surface of the inner cap at intervals.

According to still another aspect of the present invention, an endoscope according to the present invention includes an endoscope main body; a guide cap that is mounted to be fixed to a front end of the endoscope main body when inserting the endoscope main body into a human body and slides to protrude toward the front of the endoscope main body when withdrawing the endoscope main body inserted into the human body; and a guide wire which passes through a wire channel formed in the endoscope main body to make the guide cap slide and is provided with a catching arm to be rotatable forward, and a catching hook caught by the catching arm may be formed at the front end of the guide cap to be bent inward.

The catching arm may rotate to be inclined forward when the guide cap slides forward, and may rotate to be inclined backward when the guide cap slides backward.

A hook groove may be formed on the outside of the catching hook, and the catching portion is caught by the hook groove in a status in which the catching arm rotates to be inclined backward.

A plurality of catching arms may be provided with at the front end of the guide wire to spread radially.

An outer cap may be mounted on the front end of the endoscope main body, and the guide cap may slide on the inside of the outer cap.

The rear end of the outer cap is fixed to the front end of the endoscope main body, such that the rear end of the guide cap which slides backward may be supported.

A locking protrusion may be provided on the outer surface of the guide cap, the locking protrusion being selectively caught by catching grooves formed on the inner surface of the outer cap at intervals.

The outer cap may be provided with a supporting means which supports the rear end of the guide cap, in a status in which the guide cap slides forward.

The supporting means may be a stopper that is rotatably and elastically supported on the inner surface of the guide cap.

An inner cap may be mounted on the front end of the endoscope main body, the guide cap sliding on the outside of the inner cap.

According to the present invention, the cap coupled to the front end of the endoscope slides forward at the time of insertion of the endoscope, and the cap having the long length is mounted from the front end of the endoscope to allow the further smooth insertion of the endoscope, which makes it possible to minimize the time taken for insertion.

Also, because the cap coupled to the front end of the endoscope slides backward when withdrawing the endoscope, it is possible to take pictures while pushing the folding inner walls inside the human body away by the cap, and thus, it is possible to increase the detection rate of the polyp.

Further, by adjusting the length of the cap depending on various conditions of the practitioner during the endoscopy, the practitioner can more easily insert the endoscope and it is possible to enhance the detection rate of polyp.

DETAILED DESCRIPTION

Although the present invention may make various changes and may have several embodiments, specific embodiments will be illustrated in the accompanying drawings and described in the detailed description in detail. However, this is not intended to limit the present invention to specific embodiments, and should be understood to include all changes, equivalents and substitutes that are included within the spirit and scope of the present invention.

The terms used in this application are used for simply describing specific embodiments and are not intended to limit the present invention. The singular expressions include plural expressions, unless meaning them in a contextually clearly different manner. In this application, terms such as "including" or "having" should be understood as specifying that features, numbers, steps, operations, constituent elements, components or a combination thereof described in the specification are present, rather than excluding in advance the possibility of the presence or addition of one or more other features, numbers, steps, operations, constituent elements, components or combinations thereof.

Hereinafter, an embodiment of the endoscope according to the present invention will be described in detail with reference to the accompanying drawings.

Figure 1:
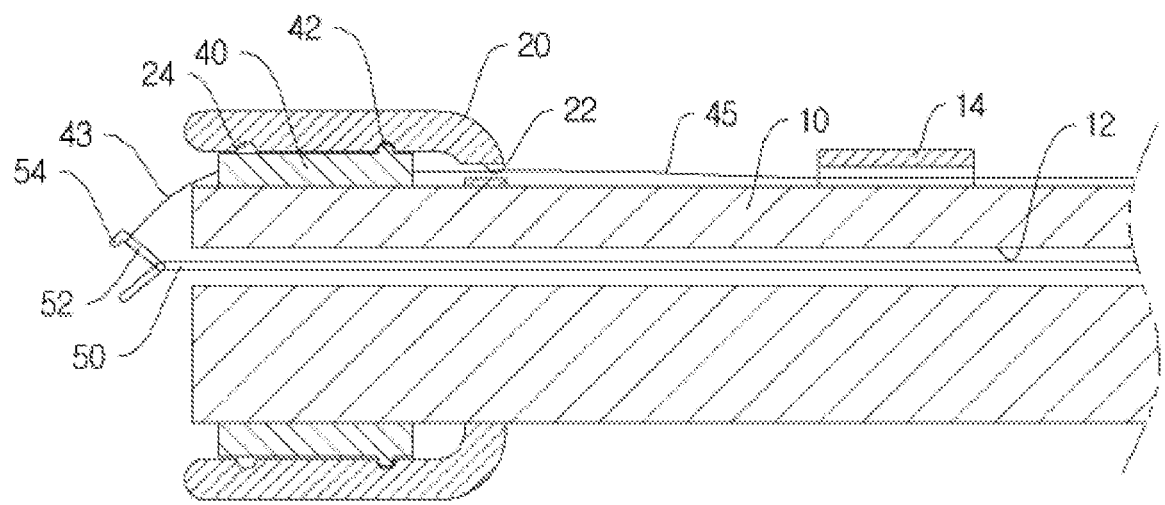
FIG. 1 is a cross-sectional view schematically illustrating an endoscope according to an embodiment of the present invention.
Figure 2:
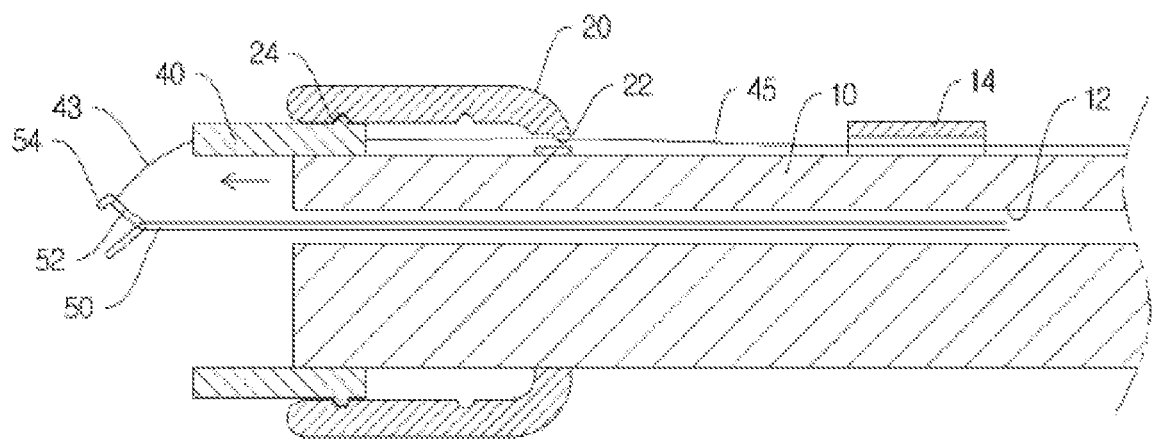
FIG. 2 is a cross-sectional view schematically illustrating a status in which a guide cap slides forward according to the embodiment illustrated in FIG. 1.

FIG. 1 is a cross-sectional view schematically illustrating an endoscope according to an embodiment of the present invention, and FIG. 2 is cross-sectional view schematically illustrating a status in which the guide cap slides forward according to the embodiment illustrated in FIG. 1.

According to the illustrated configuration, the endoscope according to the present invention may include a guide cap 40. The guide cap 40 is mounted to be fixed to a front end of the endoscope main body 10 when inserting the endoscope main body 10 into the human body, and slides to protrude to the front of the endoscope main body 10 when withdrawing the endoscope main body which is inserted into the human body 10.

The endoscope main body 10 is inserted and withdrawn in order to observe and take pictures of the interior of the human body. Although it is not specifically illustrated in the drawings, a camera, a light source or the like may be mounted on the front end of the endoscope main body 10 to take pictures of the interior of the human body.

The endoscope main body 10 has an approximately elongated tubular shape, and a wire channel 12 through which a guide wire 50 to be described later penetrates is formed inside the endoscope main body 10. The wire channel 12 is continued from the front end to the rear end of the endoscope main body 10, and the guide wire 50 is movable back and forth inside the wire channel 12.

Further, a wire supporting rib 14 is provided on the outer surface of the endoscope main body 10, and a pulling wire 45 to be described later is supported to penetrate through the wire supporting rib 14. The wire supporting rib 14 allows the pulling wire 45 continuing from the front end to the rear end of the endoscope main body 10 to be inserted and withdrawn together with endoscope main body 10, while maximally being in close contact with the endoscope main body 10. Further, a plurality of wire supporting ribs 14 may be provided with along the lengthwise direction of the endoscope main body 10 at regular intervals.

Meanwhile, an outer cap 20 is mounted to the front end of the endoscope main body 10 so that the guide cap 40 slides inside the outer cap. The outer cap 20 is a portion that is mounted so that the guide cap 40 smoothly slides at the front end of the endoscope main body 10 is mounted, and the outer cap 20 is mounted to cover the guide cap 40. Here, the rear end of the outer cap 20 is fixed to the front end of the endoscope main body 10, and the front end is formed to be spaced apart from the endoscope main body 10 by a predetermined distance. Thus, the rear end of the guide cap 40 can be supported by the outer cap 20 and can slide in a status in which its outside is supported by the outer cap 20.

A wire hole 22 is formed at the rear end of the outer cap 20, and the pulling wire 45 penetrates through the wire hole 22. Further, catching grooves 24 are formed on the inner surface of the outer cap 20 at predetermined intervals. The locking protrusion 42 of the guide cap 40 is selectively caught by the catching grooves 24. The two catching grooves 24 are formed so that each one is positioned at the front and back. When the endoscope main body 10 is inserted into the human body, the locking protrusion 42 is caught by the back catching groove 24, and thereafter, when the endoscope main body 10 is withdrawn, the locking protrusion 42 is caught by the front catching groove 24.

The guide cap 40 is made of a transparent material, and serves to enhance the detection rate of polyp by pushing the inner wall of the folding large intestine away, while sliding to protrude to the front of the endoscope main body 10. In this embodiment, the guide cap 40 is illustrated as sliding between the endoscope main body 10 and the outer cap 20, but not necessarily limited thereto, and only the guide cap 40 may slide, while being mounted to the front end of the endoscope main body 10.

A locking protrusion 42 selectively caught by the locking grooves 24 is formed to protrude from the outer surface of the guide cap 40. The locking protrusion 42 is formed on the outer surface rear end of the guide cap 40. The locking protrusion 42, for example, may be formed to have an approximately hemispherical shape, and may be formed in various shapes.

Further, an interlocking wire 43 is connected to the front end of the guide cap 40. The interlocking wire 43 is connected to the guide cap 40 and hooked by the guide wire 50 at both ends, thereby making the guide cap 40 also slide, when the guide wire 50 is made slide forward. In the present embodiment, although the interlocking wire 43 has been suggested as a connecting means been the guide cap 40 and guide wire 50, but not necessarily limited to this, and any configuration such as a separate interlocking member can be adopted as long as it is possible to connect both of the guide cap 40 and guide wire 50.

Further, the pulling wire 45 is connected to the rear end of the guide cap 40. The pulling wire 45 is a portion that pulls the guide cap 40 when a user causes the guide cap 40, which slid forward, to slide backward.

Meanwhile, as described above, the guide wire 50 is a portion that passes through the wire channel 12, and is connected through the guide cap 40 by hooking the interlocking wire 43 to serve to make the guide cap 40 slide. A pair of catching arms 52 is rotatably coupled to the front end of the guide wire 50. The pair of catching arms 52 rotate each other in a direction of approaching or moving away from each other, and a catching portion 54 for being caught by the interlocking wire 43 is formed at the front end of the catching arm 52 positioned on the side closer to the guide cap 40, of the catching arms 52. The catching portion 54 may be formed to orthogonally extend from the front end of the catching arm 52.

Here, the catching arm 52 having a configuration, by which the interlocking wire 43 is caught, is only an example, and any configuration capable of being interlocked with the interlocking wire 43 may be adopted. Further, the interlocking wire 43 may be connected to several parts of guide cap 40, rather than being connected only to a part of the guide cap 40. Meanwhile, when the guide wire 50 slides forward as illustrated in FIG. 2 in a state where the interlocking wire 43 is caught by the catching portion 54 of the catching arm 52, the guide cap 40 slides forward inside the outer cap 20 in conjunction with the sliding.

Figure 3:
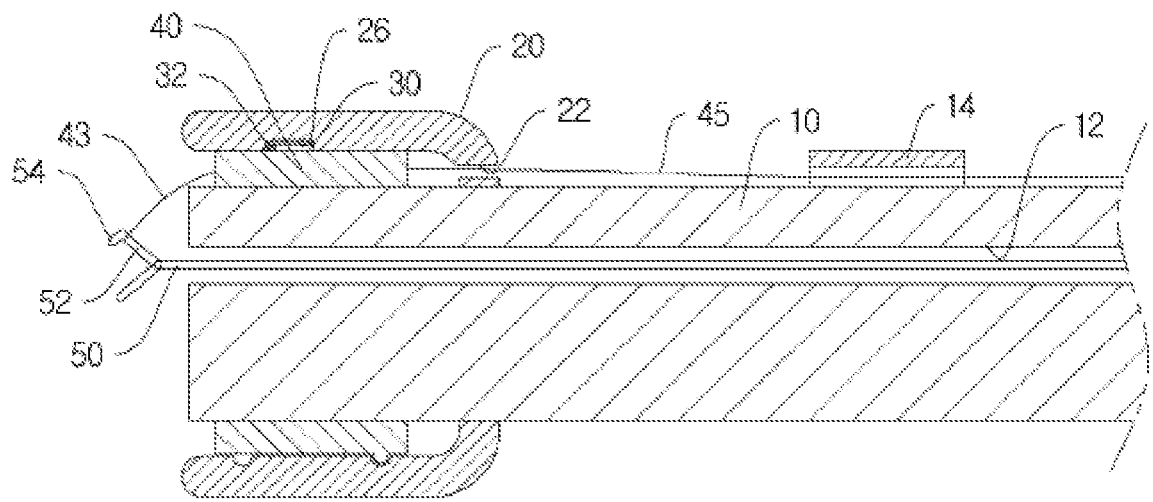
FIG. 3 is a cross-sectional view schematically illustrating an endoscope according to an embodiment of the present invention.
Figure 4:
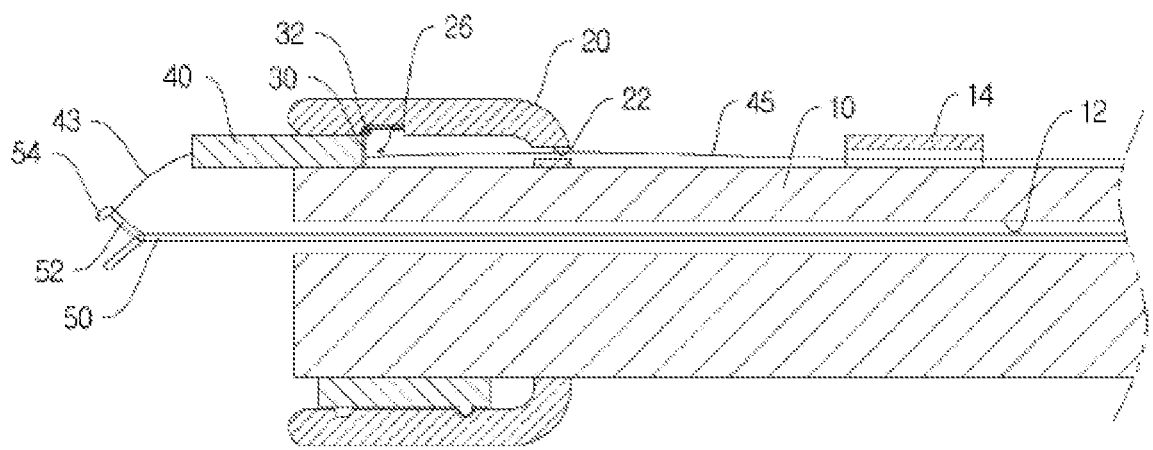
FIG. 4 is a cross-sectional view schematically illustrating a status in which the guide cap slides forward according to the embodiment illustrated in FIG. 3.

Next, FIG. 3 is a cross-sectional view schematically illustrating the endoscope according to an embodiment of the present invention, and FIG. 4 is a cross-cross-sectional view schematically illustrating a status in which the guide cap slides forward according to the embodiment illustrated in FIG. 3.

According to the illustrated configuration, the endoscope according to the present embodiment may further includes a supporting means for supporting the rear end of the guide cap 40 in a status in which the guide cap 40 slides forward.

A stopper 30 is rotatably and elastically supported on the inner surface of the guide cap 40, as a supporting means. One end of the stopper 30 is rotatably fixed to a seating groove 26 formed on the inner surface of the outer cap 20, an elastic member 32 is provided on the rotation axis of the stopper 30, and the stopper 30 provides an elastic force in a direction in which the guide cap 40 slides forward. That is, the stopper 30 is initially located in the seating groove 26 by being pushed by the guide cap 40, in the status in which the guide cap 40 slides backward, and thereafter, when the guide cap 40 slides forward, the stopper 30 supports the rear end of the guide cap 40, while being rotated by the elastic force. Accordingly, as illustrated in FIG. 4, the guide cap 40 can be supported by the stopper 30, without being pushed backward in the state of sliding forward.

Figure 5:
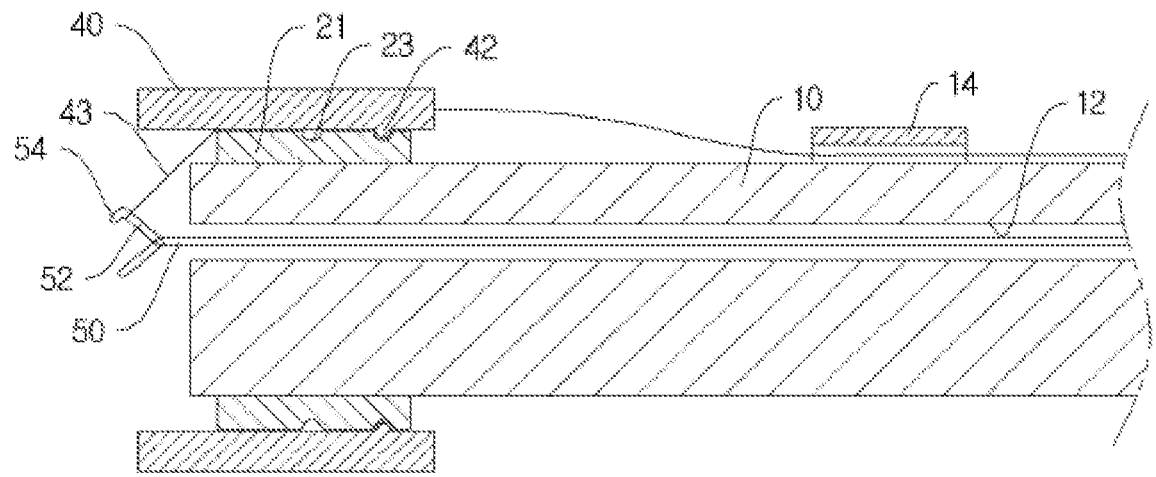
FIG. 5 is a cross-sectional view schematically illustrating an endoscope according to another embodiment of the present invention.
Figure 6:
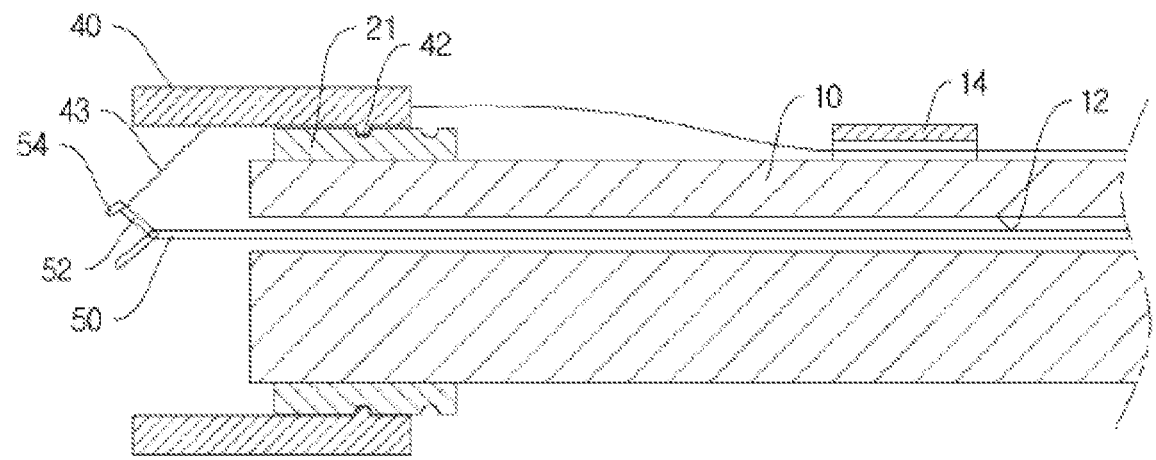
FIG. 6 is a cross-sectional view schematically illustrating a status in which a guide cap slides forward according to the embodiment illustrated in FIG. 5.

FIG. 5 is a cross-sectional view schematically illustrating the endoscope according to another embodiment of the present invention, and FIG. 6 is a cross-sectional view schematically illustrating a status in which the guide cap slides forward according to the embodiment illustrated in FIG. 5.

According to the illustrated configuration, in the present embodiment, the guide cap 40 is configured to slide on the outside of the inner cap 21 mounted on the front end of the endoscope main body 10, rather than sliding on the inside of the outer cap 20. At this time, a locking protrusion 42 is provided on the inner surface of the guide cap 40, and the locking protrusion 42 is selectively caught by the catching grooves 23 of the inner cap 21. When the guide cap 40 slides on the outside of the inner cap 21 in this way, as compared to a case of sliding on the inside of the outer cap 20, sliding can be more smoothly performed under a condition of small frictional force.

Figure 7:
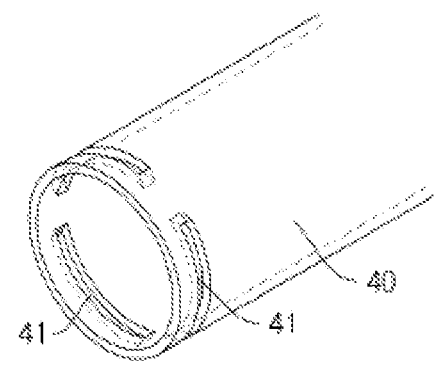
FIG. 7 is a perspective view illustrating another embodiment of the guide cap.

Next, FIG. 7 is a perspective view illustrating another example of the guide cap.

According to the illustrated configuration, in this embodiment, cap holes 41 are formed at the front end of the guide cap 40. A plurality of cap holes 41 is formed at the front end of the guide cap 40 in the circumferential direction at regular intervals. The cap holes 41 are portions by which the catching portion 54 of the guide wire 50 is caught. Because the plurality of cap holes 41 is formed in the circumferential direction, it is possible to increase the chances that the catching portion 54 is caught by the cap holes 41, regardless of the direction of rotation of the guide wire 50.

As described above, when the endoscope according to the present invention is inserted into the human body, the guide cap 40 lengthily slides forward and protrudes to maintain a condition of being easily inserted. However, in some cases, when inserting the endoscope into the human body, the endoscope slides backward, and the visual field can be sufficiently ensured, thereby making it possible to minimize the time taken for insertion. Further, when withdrawing the endoscope from the interior of the human body, because the guide cap 40 shortly slides forward and protrudes, it is possible to taking pictures and observing, while pushing the winding inner walls of the human body away by the guide cap 40, thereby making it possible to enhance the detection rate of polyps.

Figure 8:
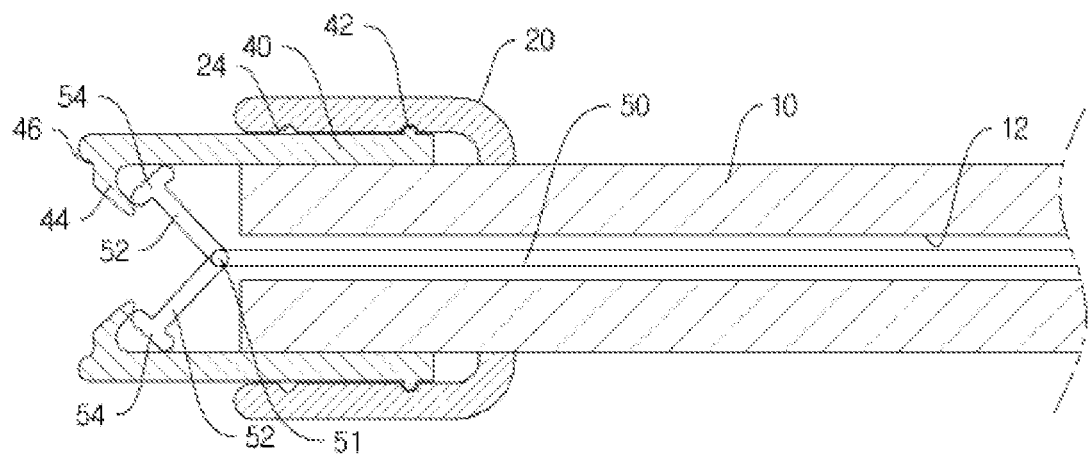
FIG. 8 is a cross-cross-sectional view schematically illustrating a status in which a guide wire supports the inside of the guide cap according to still another embodiment of the present invention.
Figure 9:
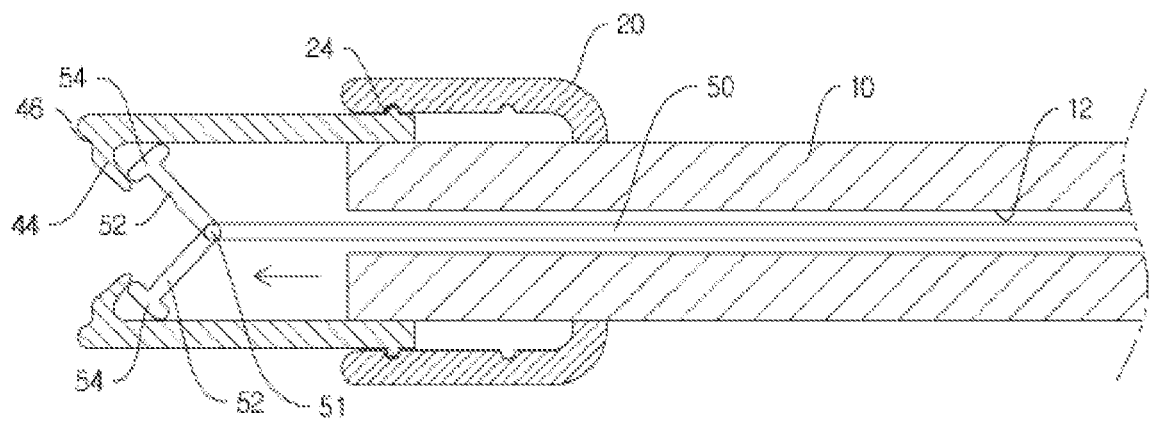
FIG. 9 is a cross-sectional view schematically illustrating a status in which the guide cap slides forward.
Figure 10:
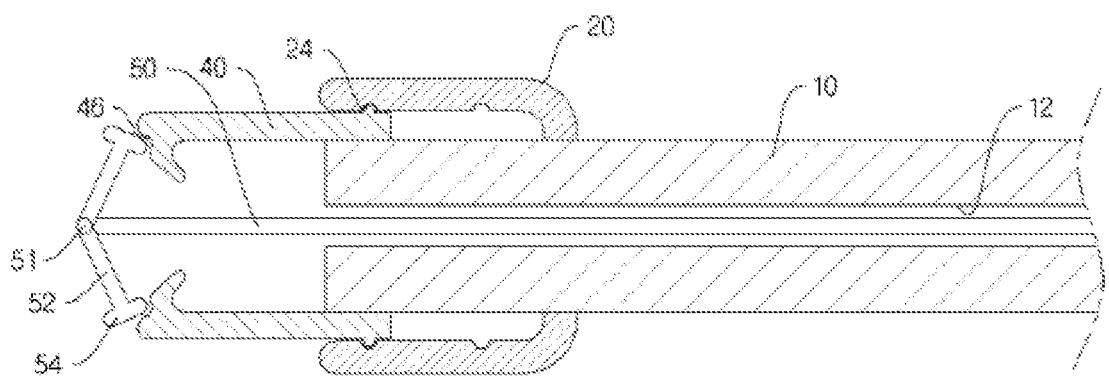
FIG. 10 is a cross-sectional view schematically illustrating a status in which the guide wire supports the outside of the guide cap.
Figure 11:
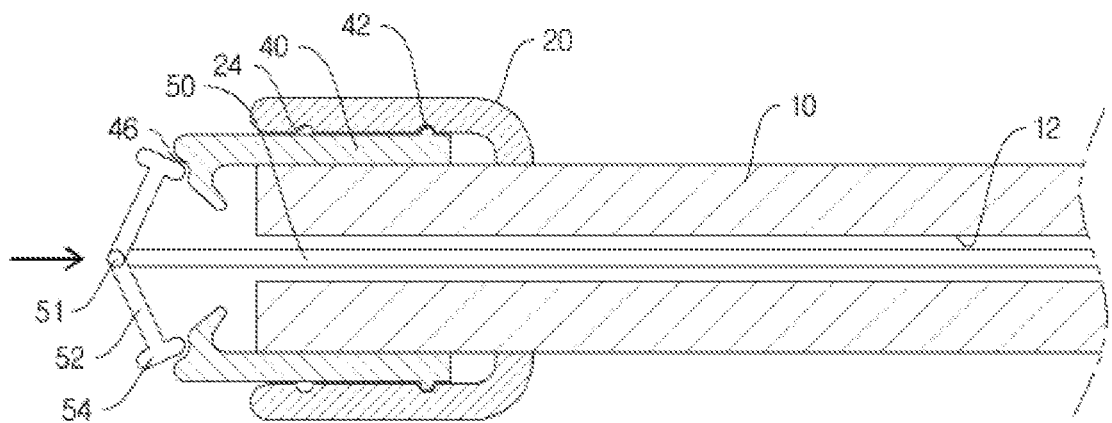
FIG. 11 is a cross-sectional view schematically illustrating a status in which the guide cap slides backward.

FIG. 8 is a cross-sectional view schematically illustrating a status in which a guide wire supports the inside of the guide cap according to still another embodiment of the present invention, FIG. 9 is a cross-sectional view schematically illustrating a status in which the guide cap slides forward, FIG. 10 is a cross-sectional view schematically illustrating a status in which the guide wire supports the outside of the guide cap, and FIG. 11 is a cross-sectional view schematically illustrating a status in which the guide cap slides backward.

According to the illustrated configuration, an endoscope according to the present invention may include an endoscope main body 10; a guide cap 40 that is mounted to be fixed to a front end of the endoscope main body 10 when inserting the endoscope main body 10 into a human body and slides to protrude toward the front of the endoscope main body 10 when withdrawing the endoscope main body 10 inserted into the human body; and a guide wire 50 which passes through a wire channel 12 formed in the endoscope main body 10 to make the guide cap 40 slide and in which a catching arm 52 is rotatably provided to face forward or backward. Further, a catching hook 44 caught by the catching arm 52 may be formed at the front end of the guide cap 40 to be bent inward.

The endoscope main body 10, the wire channel 12 and the guide wire 50 have the same configuration as the above-described embodiment of the present invention, and the specific description thereof will be replaced by the description of the above-described embodiment.

Meanwhile, an outer cap 20 is mounted to the front end of the endoscope main body 10 so that the guide cap 40 slides on the inside. The outer cap 20 is a portion that is mounted so that the guide cap 40 smoothly slides at the front end of the endoscope main body 10, and the outer cap 20 is mounted to cover the guide cap 40. Here, the rear end of the outer cap 20 is fixed to the front end of the endoscope main body 10, and the front end thereof is formed to be spaced apart from the endoscope main body 10 by a predetermined distance. Thus, the guide cap 40 may be supported, at the rear end, on the outer cap 20 and can slide in a status in which the outside is supported by the outer cap 20.

Catching grooves 24 are formed on the inner surface of the outer cap 20 at a predetermined interval. The locking protrusion 42 of the guide cap 40 is selectively caught by the catching grooves 24. The two catching grooves 24 are formed so that each one is positioned at the front and back.

When the endoscope main body 10 is inserted into the human body, the locking protrusion 42 is caught by the back catching groove 24, and thereafter, when the endoscope main body 10 is withdrawn, the locking protrusion 42 is caught by the front catching groove 24.

The guide cap 40 is made of a transparent material, and serves to enhance the detection rate of polyps by pushing the inner wall of the winding large intestine away, while sliding to protrude to the front of the endoscope main body 10. In this embodiment, the guide cap 40 is illustrated as sliding between the endoscope main body 10 and the outer cap 20, but not necessarily limited thereto, and only the guide cap 40 may slide, while being mounted to the front end of the endoscope main body 10.

A locking protrusion 42 selectively caught by the locking grooves 24 is formed to protrude from the outer surface of the guide cap 40. The locking protrusion 42 is formed on the outer surface rear end of the guide cap 40. The locking protrusion 42, for example, may be formed to have an approximately hemispherical shape, and may be formed in various shapes.

Further, a catching hook 44 for being caught by the catching arm 52 is formed at the front portion end of the guide cap 40 to be bent inward. The catching hook 44 is formed by machining the front end portion of the catching arm 52 and preferably has a hook shape so that the catching arms 52 can be caught. The catching hook 44 may also be formed entirely at the front end portion of the guide cap 40, and a plurality of catching hooks 44 may be formed in the circumferential direction at a predetermined interval.

In the above, while the description has been given of a case where the guide cap 40 is mounted on the front end of the endoscope main body 10 to slide, it is not limited thereto, and the guide cap 40 may be separately provided and coupled so as to be easily attached to and detached from the front end of the endoscope main body 10.

Meanwhile, as described above, the guide wire 50 is a portion that passes through the wire channel 12, and serves to make the guide cap 40 slide. A plurality of catching arms 52 is coupled to the front end of the guide wire 50 to be rotatable about the rotation pin 51. The plurality of catching arms 52 rotate each other in a direction of approaching or moving away from each other, and the catching portion 54 may be formed to orthogonally extend from the front end of the catching arm 52. When pushing the guide wire 50 forward, in a status in which the catching portion 54 of the catching arm 52 is caught on the inside of the catching hook 44, the guide cap 40 slides forward in conjunction with the pushing. Further, since the guide cap 40 is pushed, while the catching arms 52 is supported so as to be inclined toward the front, the guide cap 40 can more easily slide.

Here, the catching arm 52 having a configuration of being caught by the catching hook 44 is only an example, and any configuration capable of being caught by the catching hook 44 may be adopted.

Further, since it is two-dimensionally displayed in this embodiment, the two catching arms 52 are provided, but is not limited thereto, a plurality of catching arms 52 may be provided with at the front end of the guide wire 50 to spread radially.

Next, referring to FIGS. 10 and 11, the guide wire 50 may be further pushed forward in order to make the guide cap 40 slide again. Then, the catching arm 52 rotates to be inclined toward the back, and the rotated catching portion 54 is caught on the hook grooves 46 formed on the outside of the catching hook 44. When pulling the guide wire 50 backward in this state, the guide cap 40 can smoothly slide backward.

Although a rotating structure of the catching arm 52 of the guide wire 50 described above has not been specifically described, for example, it may be achieved by providing a elastic member (not illustrated) in the rotation pin 51 and providing a separate stopper (not illustrated) on the side of the guide wire 50 to adjust the rotation angle of the catching arms 52.

Furthermore, although the description has been given of a case where the catching arm 52 of the guide wire 50 can rotate forward or backward, the catching arm 52 may be configured to rotate forward. The reason is that, because the guide cap 40 maintains a state of sliding forward in the process in which the endoscope is withdrawn, the operation of making the guide cap 40 side backward may also be performed after withdrawing the endoscope.

Figure 12:
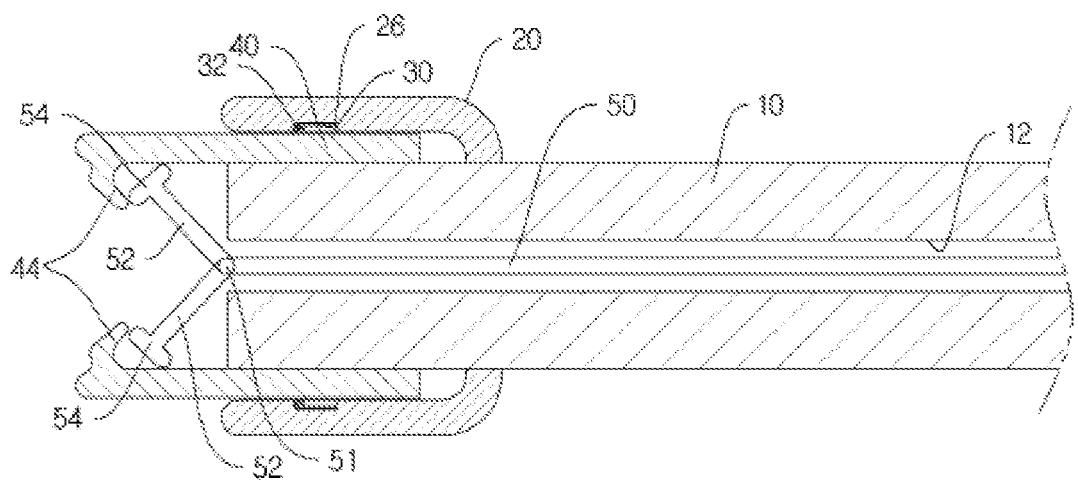
FIGS. 12 and 13 are operational status diagrams illustrating a status in which a stopper supports the rear end of the guide cap.
Figure 13:
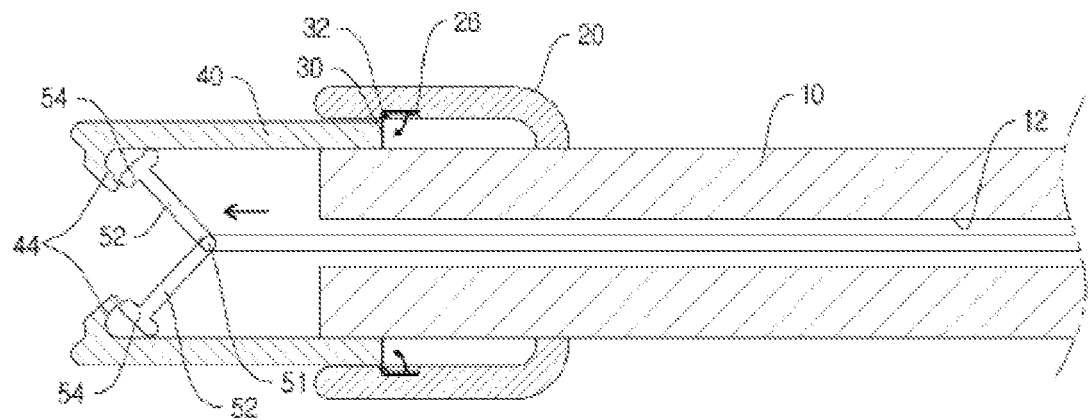

Next, FIGS. 12 and 13 are operational state diagram illustrating a status in which the stopper supports the rear end of the guide cap.

According to the illustrated configuration, the endoscope according to the present embodiment may further includes a supporting means for supporting the rear end of the guide cap 40 in a status in which the guide cap 40 slides forward.

A stopper 30 is rotatably and elastically supported on the inner surface of the guide cap 40, as a supporting means. One end of the stopper 30 is rotatably fixed to a seating groove 26 formed on the inner surface of the outer cap 20, an elastic member 32 is provided on the rotation axis of the stopper 30, and the stopper 30 provides an elastic force in a direction in which the guide cap 40 slides forward. That is, the stopper 30 is initially located in the seating groove 26 by being pushed by the guide cap 40, in the status in which the guide cap 40 slides backward, and thereafter, when the guide cap 40 slides forward, the stopper 30 supports the rear end of the guide cap 40, while being rotated by the elastic force. Accordingly, as illustrated in FIG. 13, the guide cap 40 can be supported by the stopper 30, without being pushed backward in the state of sliding forward.

Figure 14:
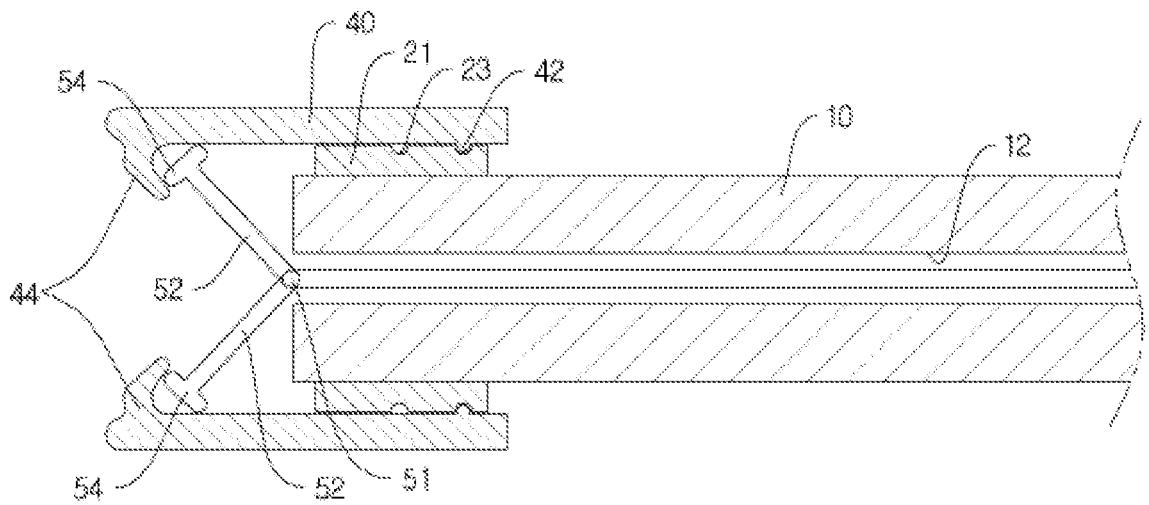
FIG. 14 is a cross-cross-sectional view schematically illustrating a status in which the guide wire supports the inside of the guide cap according to still another embodiment of the present invention.
Figure 15:
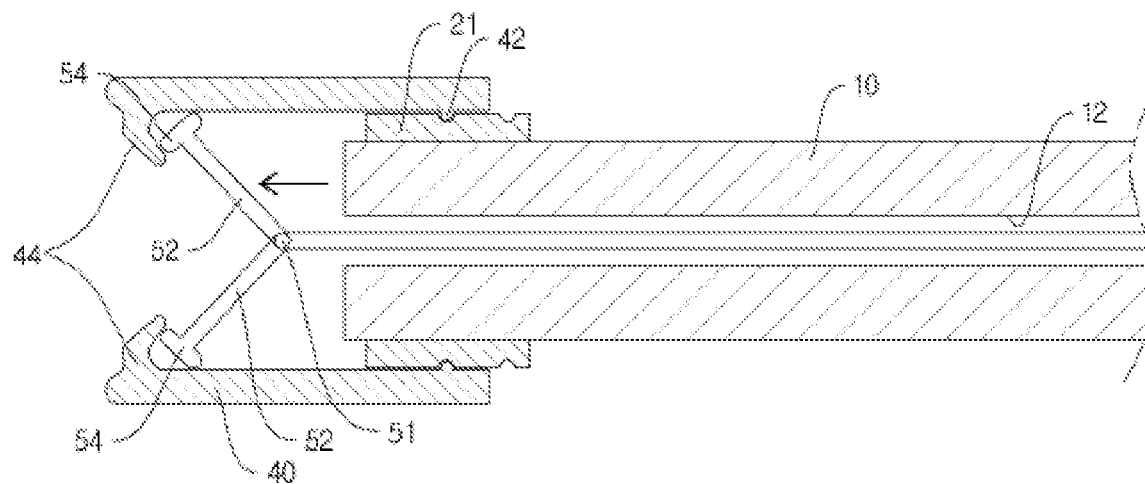
FIG. 15 is a cross-sectional view schematically illustrating a status in which the guide cap slides forward.

Hereinafter, en endoscope according to another embodiment of the present invention will be described referring to the drawings. FIG. 14 is a cross-cross-sectional view schematically illustrating a status in which the guide wire supports the inside of the guide cap according to still another embodiment of the present invention, and FIG. 15 is a cross-sectional view schematically illustrating a status in which the guide cap slides forward.

According to the illustrated configuration, in the present embodiment, the guide cap 40 is configured to slide on the outside of the inner cap 21 mounted on the front end of the endoscope main body 10, rather than sliding on the inside of the outer cap 20. At this time, a locking protrusion 42 is provided on the inner surface of the guide cap 40, and the locking protrusion 42 is selectively caught by the catching grooves 23 of the inner cap 21. When the guide cap 40 slides on the outside of the inner cap 21 in this way, as compared to a case of sliding on the inside of the outer cap 20, the sliding can be more smoothly performed under a condition of small frictional force.

Further, in this embodiment, because the configuration of operation of the catching arm 52 of the guide wire 50 is the same as in the above-described embodiment, the detailed description thereof will not be provided.

As described above, when in the endoscope according to the present invention is inserted into the human body, the guide cap 40 protrudes long forward to maintain a condition of being easily inserted. However, in some cases, when the endoscope is inserted into the human body, the guide cap slides backward, and the visual field may be sufficiently ensured, and thus, it is possible to minimize the time taken for insertion. Further, when withdrawing the endoscope from the endoscope main body, because the guide cap 40 shortly slides forward and protrudes, it is possible to take pictures, while pushing the winding inner walls of the human body away by the guide cap 40, thereby enhancing the detection rate of the endoscope.

While the embodiments of the present invention have been described above in detail, the scope of the present invention is not limited thereto, and various modifications or improvements of those skilled in the art using the basic concepts of the present invention that are defined in the following claims also belong to the scope of the present invention.

What is claimed is:

1. An endoscope comprising:
   an endoscope main body;
   an outer cap mounted on a front end of the endoscope main body;
   a guide cap disposed between the outer cap and the front end of the endoscope main body, and configured to slide between a first position at which the guide cap is placed inside the outer cap and a second position at which the guide cap protrudes distally from a front of the endoscope main body;
   a pulling wire coupled to a rear end of the guide cap and disposed outside the endoscope main body such that the guide cap slides from the second position to the first position when the pulling wire slides backward;
   a supporter provided on an inner surface of the outer cap and configured to impede sliding of the guide cap from the second position to the first position by supporting a rear side of the guide cap while the guide cap is at the second position; and
   a guide wire which is connected to the guide cap through a guide channel formed in the endoscope main body to make the guide cap slide forward.

2. The endoscope of claim 1, wherein the supporter comprises a stopper mounted on the inner surface of the outer cap in a rotatable manner and configured to rotate by an elastic force when the guide cap is at the second position.

3. The endoscope of claim 1, further comprising:
   an interlocking wire which connects the guide cap and the guide wire.

4. The endoscope of claim 1, wherein the guide wire is connected with the guide cap such that the guide cap slides forward when the guide wire moves forward.

5. The endoscope of claim 4, wherein the guide wire has a catching arm having a catching portion formed at a front end of the catching arm, and
   wherein the catching portion of the catching arm is connected to the guide cap by an interlocking wire.

6. The endoscope of claim 4, wherein the guide wire has a catching arm having a catching portion formed at a front end of the catching arm, and a plurality of cap holes are formed at the front end of the guide cap in an outer peripheral direction, the catching portion being caught by the plurality of cap holes.

* * * * *